(12) United States Patent
McLaughlin et al.

(10) Patent No.: US 11,491,019 B2
(45) Date of Patent: *Nov. 8, 2022

(54) EXPANDABLE INTERVERTEBRAL IMPLANT

(71) Applicant: GLOBUS MEDICAL, INC., Audubon, PA (US)

(72) Inventors: Colm McLaughlin, Glenside, PA (US); Jason Zappacosta, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 198 days.

This patent is subject to a terminal disclaimer.

(21) Appl. No.: 16/901,041

(22) Filed: Jun. 15, 2020

(65) Prior Publication Data

US 2020/0375753 A1 Dec. 3, 2020

Related U.S. Application Data

(63) Continuation of application No. 15/808,180, filed on Nov. 9, 2017, now Pat. No. 10,709,569.

(51) Int. Cl.
*A61F 2/44* (2006.01)
*A61B 17/86* (2006.01)
(Continued)

(52) U.S. Cl.
CPC ............ *A61F 2/4425* (2013.01); *A61B 17/86* (2013.01); *A61F 2/30749* (2013.01);
(Continued)

(58) Field of Classification Search
CPC .. A61F 2/4425; A61F 2002/443; A61F 2/445; A61F 2/447
See application file for complete search history.

(56) References Cited

U.S. PATENT DOCUMENTS 2,888,099 A 5/1959 Hoffmann
5,522,899 A * 6/1996 Michelson .............. A61F 2/447
606/279

(Continued)

FOREIGN PATENT DOCUMENTS

EP 3031424 A1 6/2016
JP 2016-508412 A 3/2016
(Continued)

*Primary Examiner* — Anu Ramana

(57) ABSTRACT

An implant including first and second end plates, each of which defines at least one anterior ramped surface and at least one posterior ramped surface. A posterior actuator is positioned between the first and second end plates and has guiding ramp surfaces which correspond with the posterior ramped surfaces. An anterior actuator is positioned between the first and second end plates and guiding ramp surfaces which correspond with the anterior ramped surfaces. An actuator assembly extends between the posterior actuator and the anterior actuator and is configured to selectively move the posterior actuator and the anterior actuator simultaneously, move posterior actuator independently of the anterior actuator, or move the anterior actuator independently of the posterior actuator.

20 Claims, 8 Drawing Sheets

(51) Int. Cl.
*A61F 2/30* (2006.01)
*A61F 2/46* (2006.01)

(52) U.S. Cl.
CPC ............ *A61F 2/447* (2013.01); *A61F 2/4455* (2013.01); *A61F 2/442* (2013.01); *A61F 2/4603* (2013.01); *A61F 2/4611* (2013.01); *A61F 2002/30261* (2013.01); *A61F 2002/30266* (2013.01); *A61F 2002/30329* (2013.01); *A61F 2002/30331* (2013.01); *A61F 2002/30365* (2013.01); *A61F 2002/30367* (2013.01); *A61F 2002/30405* (2013.01); *A61F 2002/30411* (2013.01); *A61F 2002/30433* (2013.01); *A61F 2002/30471* (2013.01); *A61F 2002/30507* (2013.01); *A61F 2002/30523* (2013.01); *A61F 2002/30537* (2013.01); *A61F 2002/30538* (2013.01); *A61F 2002/30556* (2013.01); *A61F 2002/30579* (2013.01); *A61F 2002/30593* (2013.01); *A61F 2002/30622* (2013.01); *A61F 2002/30624* (2013.01); *A61F 2002/443* (2013.01); *A61F 2002/4625* (2013.01); *A61F 2002/4627* (2013.01)

(56) References Cited

U.S. PATENT DOCUMENTS

| | | | |
|---|---|---|---|
| 8,366,777 B2* | 2/2013 | Matthis | A61F 2/4465 |
| | | | 623/17.11 |
| 8,597,360 B2 | 12/2013 | McLuen et al. | |
| 9,259,249 B2* | 2/2016 | Zappacosta | A61B 17/7067 |
| 9,320,610 B2* | 4/2016 | Alheidt | A61F 2/4611 |
| 9,358,123 B2 | 6/2016 | McLuen et al. | |
| 9,445,919 B2 | 9/2016 | Palmatier et al. | |
| 9,750,618 B1 | 9/2017 | Daffinson et al. | |
| 9,801,734 B1 | 10/2017 | Stein et al. | |
| 9,987,146 B1 | 6/2018 | Lentner et al. | |
| 10,022,239 B1 | 7/2018 | Lentner et al. | |
| 10,327,917 B2* | 6/2019 | Glerum | A61F 2/447 |
| 2005/0125061 A1* | 6/2005 | Zucherman | A61F 2/4425 |
| | | | 623/17.11 |
| 2008/0147193 A1* | 6/2008 | Matthis | A61F 2/4465 |
| | | | 623/17.16 |
| 2010/0211176 A1* | 8/2010 | Greenhalgh | A61F 2/4611 |
| | | | 623/17.15 |
| 2013/0197642 A1 | 8/2013 | Ernst | |
| 2013/0197647 A1* | 8/2013 | Wolters | A61F 2/442 |
| | | | 623/17.16 |
| 2013/0211526 A1* | 8/2013 | Alheidt | A61F 2/4611 |
| | | | 623/17.16 |
| 2014/0243982 A1 | 8/2014 | Miller | |
| 2015/0018951 A1 | 1/2015 | Loebl et al. | |
| 2016/0166396 A1 | 6/2016 | McClintock | |
| 2016/0374826 A1 | 12/2016 | Palmatier et al. | |
| 2017/0296238 A1 | 10/2017 | Snell et al. | |
| 2017/0333196 A1 | 11/2017 | Robinson | |
| 2018/0036138 A1 | 2/2018 | Robinson | |
| 2018/0110629 A1 | 4/2018 | Ewer et al. | |
| 2019/0358057 A1 | 11/2019 | McLaughlin | |

FOREIGN PATENT DOCUMENTS

| | | |
|---|---|---|
| JP | 2016-523678 A | 8/2016 |
| JP | 2018-504245 A | 2/2018 |
| WO | 2016069796 A1 | 5/2016 |
| WO | 2017040881 A1 | 3/2017 |

* cited by examiner

EXPANDABLE INTERVERTEBRAL IMPLANT

CROSS REFERENCE TO RELATED APPLICATIONS

This application is a continuation of U.S. patent application Ser. No. 15/808,180, filed on Nov. 9, 2017, the contents of which is incorporated by reference herein in its entirety for all purposes.

FIELD OF THE INVENTION

This present disclosure relates to stabilizing adjacent vertebrae of the spine by inserting an intervertebral implant, and more particularly an intervertebral implant that is adjustable in height and/or angularity and associated methods.

BACKGROUND

Bones and bony structures are susceptible to a variety of weaknesses that can affect their ability to provide support and structure. Weaknesses in bony structures have numerous potential causes, including degenerative diseases, tumors, fractures, and dislocations. Advances in medicine and engineering have provided doctors with a plurality of devices and techniques for alleviating or curing these weaknesses.

In some cases, the spinal column requires additional support in order to address such weaknesses. One technique for providing support is to insert a spacer between adjacent vertebrae.

SUMMARY

To meet this and other needs, expandable implants, systems, and methods are provided. The expandable implant may be expandable and adjustable in height and/or angularity. The implant may be inserted into an intervertebral disc space at a minimized height, and then expanded axially to restore height loss in the disc space. The implant may provide distraction as well as achieving optimal height restoration. The implant may also change in lordotic angulation independently from its expansion. This independent expansion and lordotic angulation may solve some of the problems currently encountered, such as excessive impaction during insertion, visual obstruction, and imperfect matching with patient's lordosis due to discrete increments in lordotic angulation. It will be appreciated that although generally described with respect to lordotic angulation, the implant may also be configured to provide kyphotic expansion and angulation to treat kyphosis as well.

In at least one embodiment, the present disclosure provides an implant for therapeutically separating bones of a joint. The implant includes a first end plate extending between an anterior end and a posterior end. The first end plate has a bone engaging surface, at least one anterior ramped surface and at least one posterior ramped surface on a side opposite the bone engaging surface. A second end plate extends between an anterior end and a posterior end. The second end plate has a bone engaging surface, at least one anterior ramped surface and at least one posterior ramped surface on a side opposite the bone engaging surface. A posterior actuator is positioned between the first and second end plates and has a corresponding number of first guiding ramp surfaces configured to be positioned opposite the at least one first end plate posterior ramped surface and a corresponding number of second guiding ramp surfaces configured to be positioned opposite the at least one second end plate posterior ramped surface. A pivot member is pivotally connected to each first guiding ramp surface and in sliding engagement with the respective at least one first plate posterior ramped surface and a pivot member is pivotally connected to each second guiding ramped surface and in sliding engagement with the respective at least one first plate posterior ramped surface. An anterior actuator is positioned between the first and second end plates and has a corresponding number of third guiding ramp surfaces configured to be positioned opposite the at least one first end plate anterior ramped surface and a corresponding number of fourth guiding ramp surfaces configured to be positioned opposite the at least one second end plate anterior ramped surface. A pivot member is pivotally connected to each third guiding ramp surface and in sliding engagement with the respective at least one first plate anterior ramped surface and a pivot member is pivotally connected to each fourth guiding ramped surface and in sliding engagement with the respective at least one first plate anterior ramped surface. An actuator assembly extends between the posterior actuator and the anterior actuator and is configured to selectively move the posterior actuator and the anterior actuator simultaneously, move posterior actuator independently of the anterior actuator, or move the anterior actuator independently of the posterior actuator.

In at least one embodiment, the present invention provides an implant including a first end plate extending between an anterior end and a posterior end. The first end plate defines at least one anterior ramped surface and at least one posterior ramped surface. A second end plate extends between an anterior end and a posterior end and defines at least one anterior ramped surface and at least one posterior ramped surface. A posterior actuator is positioned between the first and second end plates and has a corresponding number of first guiding ramp surfaces configured to be positioned opposite the at least one first end plate posterior ramped surface and a corresponding number of second guiding ramp surfaces configured to be positioned opposite the at least one second end plate posterior ramped surface. A pivot member is pivotally connected to each first guiding ramp surface and in sliding engagement with the respective at least one first plate posterior ramped surface and a pivot member is pivotally connected to each second guiding ramped surface and in sliding engagement with the respective at least one first plate posterior ramped surface. An anterior actuator is positioned between the first and second end plates and has a corresponding number of third guiding ramp surfaces configured to be positioned opposite the at least one first end plate anterior ramped surface and a corresponding number of fourth guiding ramp surfaces configured to be positioned opposite the at least one second end plate anterior ramped surface. A pivot member is pivotally connected to each third guiding ramp surface and in sliding engagement with the respective at least one first plate anterior ramped surface and a pivot member is pivotally connected to each fourth guiding ramped surface and in sliding engagement with the respective at least one first plate anterior ramped surface. An actuator assembly extends between the posterior actuator and the anterior actuator. The actuator assembly includes an actuator screw extending between a posterior end and an anterior end with a first external thread set proximate the posterior end and a second external thread set proximate the anterior end wherein the first and second external thread sets are oppositely handed. The posterior end of the actuator screw extends through and threadably engages a through passage in the posterior actuator. The actuator assembly further includes an actuator nut extending between a posterior end and an anterior end with a through passage extending from the posterior end to the anterior end and defining an internal thread within the through passage. The internal thread is threadably engaged with the second set of external threads. The actuator nut extends through the anterior actuator such that the actuator nut is axially fixed relative to the anterior actuator but rotatable relative thereto. Rotation of the actuator screw while the actuator nut does not rotate causes the posterior actuator and the anterior actuator to move simultaneously, rotation of the actuator screw and the actuator nut together causes the posterior actuator to move independently of the anterior actuator, and rotation of the actuator nut while the actuator screw does not rotate causes the anterior actuator to move independently of the posterior actuator.

In at least one embodiment, the implant may include one or more bearings. The bearings may be configured to connect one or both of the end plates to the actuator assembly and allow the actuator screw to rotate regardless of end plate angulation. For example, the posterior end of the actuator screw may include a ball which is supported in a spherical bearing supported by the first and second end plates. In an alternative arrangement, the implant may be provided without bearings present, such that the end plates would be free to pivot or translate without restriction.

In at least one embodiment, the disclosure provides a method of fusing adjacent vertebral bodies including inserting an implant defining a longitudinal axis extending between distal and proximal ends between bones of the joint, the implant includes a first end plate extending between an anterior end and a posterior end. The first end plate has a bone engaging surface, at least one anterior ramped surface and at least one posterior ramped surface on a side opposite the bone engaging surface. A second end plate extends between an anterior end and a posterior end. The second end plate has a bone engaging surface, at least one anterior ramped surface and at least one posterior ramped surface on a side opposite the bone engaging surface. A posterior actuator is positioned between the first and second end plates and has a corresponding number of first guiding ramp surfaces configured to be positioned opposite the at least one first end plate posterior ramped surface and a corresponding number of second guiding ramp surfaces configured to be positioned opposite the at least one second end plate posterior ramped surface. A pivot member is pivotally connected to each first guiding ramp surface and in sliding engagement with the respective at least one first plate posterior ramped surface and a pivot member is pivotally connected to each second guiding ramped surface and in sliding engagement with the respective at least one first plate posterior ramped surface. An anterior actuator is positioned between the first and second end plates and has a corresponding number of third guiding ramp surfaces configured to be positioned opposite the at least one first end plate anterior ramped surface and a corresponding number of fourth guiding ramp surfaces configured to be positioned opposite the at least one second end plate anterior ramped surface. A pivot member is pivotally connected to each third guiding ramp surface and in sliding engagement with the respective at least one first plate anterior ramped surface and a pivot member is pivotally connected to each fourth guiding ramped surface and in sliding engagement with the respective at least one first plate anterior ramped surface. An actuator assembly extends between the posterior actuator and the anterior actuator and is configured to selectively move the posterior actuator and the anterior actuator simultaneously, move posterior actuator independently of the anterior actuator, or move the anterior actuator independently of the posterior actuator. The method further includes actuating the actuator assembly after the implant is inserted to move the first and second end plates relative to one another to increase or decrease the lordotic angle or to move the first and second endplates farther apart to separate bones of the joint.

BRIEF DESCRIPTION OF THE DRAWINGS

The accompanying drawings, which are included to provide a further understanding of the present disclosure, are incorporated in and constitute a part of this specification, illustrate aspects of the present disclosure and together with the detailed description serve to explain the principles of the present disclosure. No attempt is made to show structural details of the present disclosure in more detail than may be necessary for a fundamental understanding of the present disclosure and the various ways in which it may be practiced. In the drawings.

DETAILED DESCRIPTION

Figure 1:
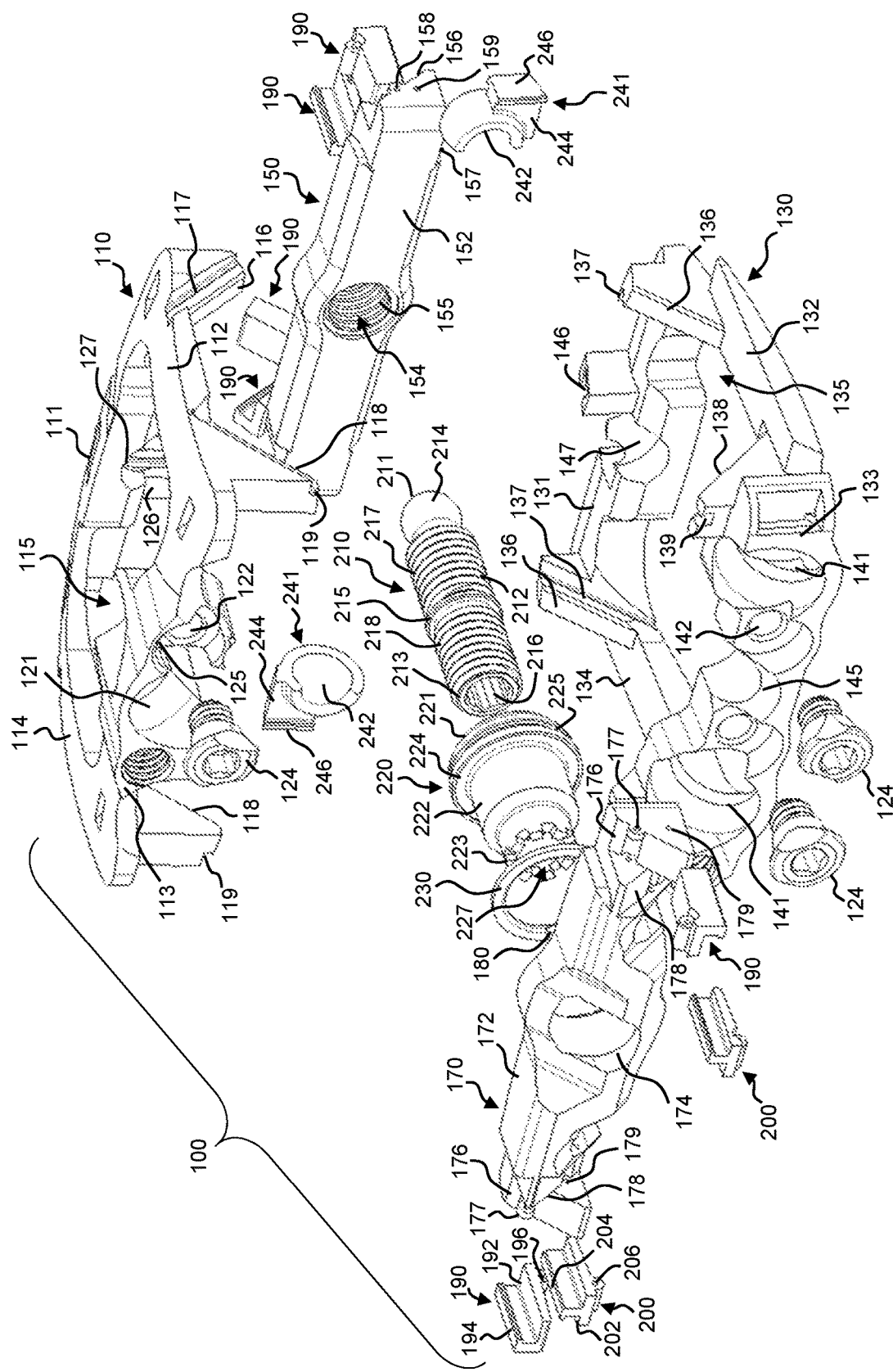
FIG. 1 is an exploded perspective view of an implant in accordance with an embodiment of the disclosure.

The aspects of the present disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the present disclosure. The examples used herein are intended merely to facilitate an understanding of ways in which the present disclosure may be practiced and to further enable those of skill in the art to practice the aspects of the present disclosure. Accordingly, the examples and aspects herein should not be construed as limiting the scope of the present disclosure, which is defined solely by the appended claims and applicable law. Moreover, it is noted that like reference numerals represent similar parts throughout the several views of the drawings.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

Implants of the disclosure allow for insertion into the intervertebral disc space at a minimized height and then expansion axially to restore height loss in the disc space. Implants of the disclosure allow continuous expansion and retraction within a range of expansion as well as achieving optimal height restoration. Implants of the disclosure may also change in lordotic angulation independently from its expansion. Implants of the disclosure may be utilized to minimize impaction during insertion, visual obstruction, and imperfect matching with a patient's lordosis due to discrete increments in lordotic angulation. Additionally, implants of the disclosure may also be collapsed and repositioned, as therapeutically indicated for the patient.

Referring to FIGS. 1-5 and 7-13, an implant 100 in accordance with an embodiment of the disclosure will be described. The implant 100 is operative, when positioned between adjacent bones of a joint, such as for example vertebrae (not shown), to stabilize a joint formed by adjacent vertebrae. The implant 100 is illustrated in an anterior interbody spacer configuration but it could also be used in other approaches, for example, such as direct lateral where coronal deformity is encountered.

Figure 2:
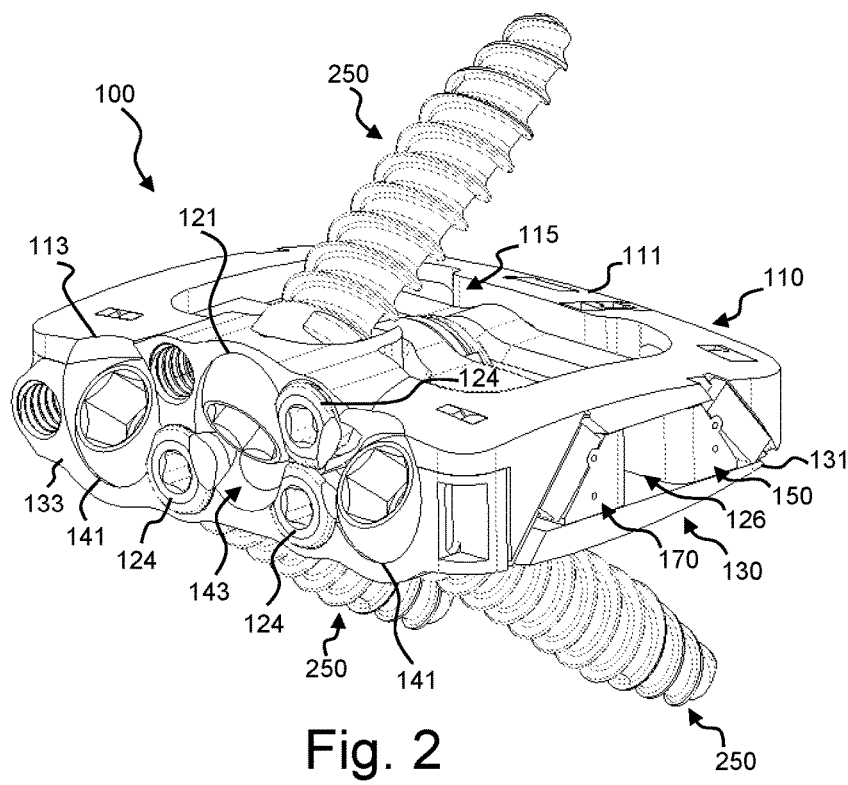
FIG. 2 is a perspective view of the implant of FIG. 1 in a compressed or reduced height configuration, together with three mounted bone screws.
Figure 3:
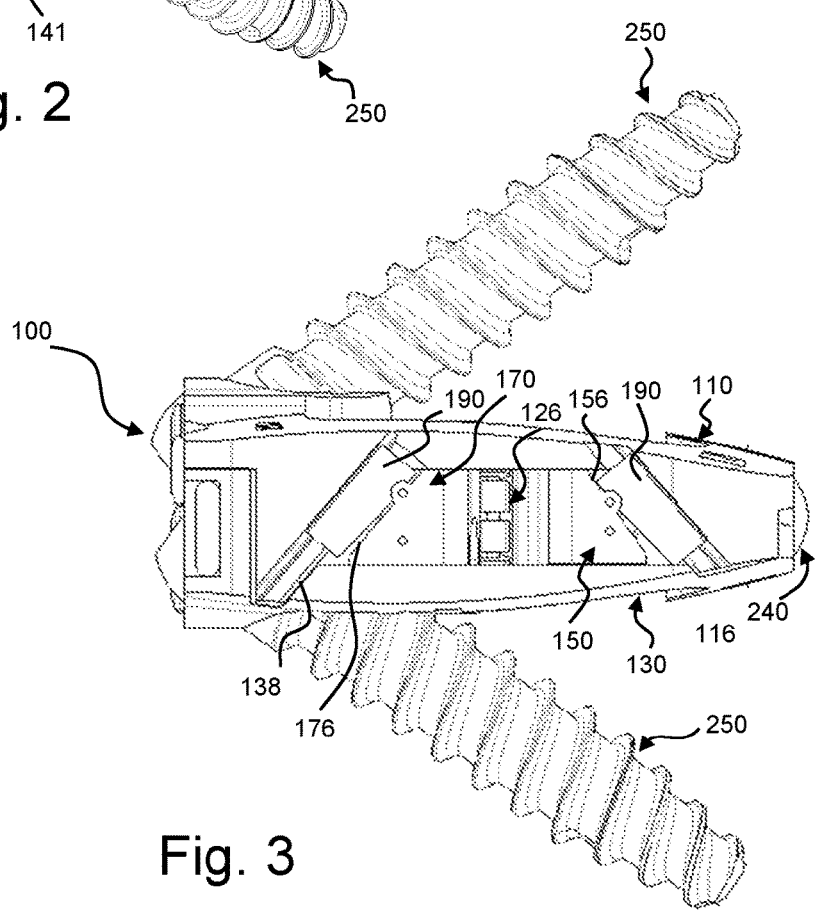
FIG. 3 is a side elevation view of the implant as shown in FIG. 2.

With reference to FIGS. 1-3, the implant 100 generally includes upper and lower endplates 110, 130, anterior and posterior actuators 150, 170, actuator pivot members 190, 200, an actuator screw 210, an actuator nut 220, a spherical bearing 240 and a thrust washer 230. In addition, the implant may include a plurality of blocking screws 124 on the endplates 110, 130 to prevent migration of the fixation screws or anchors.

The upper end plate 110 includes a posterior rail 111 and an anterior rail 113 extending between opposed side rails 112, 114. The rails 111-114 extend about a through passage 115 into a graft chamber 128 within the implant. The passage 115 allows graft material or other therapeutically beneficial material to packed into or grow into the graft chamber 128. The upper end plate 110 defines a posterior guide ramp 116 along each side rail 112, 114 and an anterior guide ramp 118 along each side rail 112, 114. Each posterior guide ramp 116 defines a groove 117 configured to receive a portion of a respective pivot member 190 and each anterior guide ramp 118 defines a groove 117 configured to receive a portion of a respective pivot member 190. As will be described hereinafter, the pivot members 190 are pivotally connected to respective actuators 150, 170 and slide along the respective ramp 116, 118 as the plates 110, 130 expand or contract.

The anterior rail 113 defines at least one bone screw/anchor through hole 121, with one such hole 121 shown in the illustrated embodiment. A blocking screw hole 122 is positioned next to the through hole 121 and is configured to receive a blocking screw 124 which may be utilized to maintain the bone screw 250 or bone anchor 260 in the through hole 121. It will be appreciated that the bone screw 250 and bone anchor 260 may be used interchangeably in the respective hole 121 and may also be substituted with any other suitable fasteners. The anterior rail 113 also defines a first hemispherical portion 125 of a driver opening 143 as shown in FIG. 2. The posterior rail 111 defines a first hemispherical portion 127 of a seat for the spherical bearing 240, as will be described hereinafter. A receiving slot 126 extends next to the hemispherical portion 127 and is configured to receive a flange 246 of one of the bearing members 241 that defines a portion of the spherical bearing 240.

The lower end plate 130 includes a posterior rail 131 and an anterior rail 133 extending between opposed side rails 132, 134. The rails 131-134 extend about a through passage 135 into the graft chamber 128 within the implant. The passage 135 again allows graft material or other therapeutically beneficial material to packed into or grow into the graft chamber 128. The lower end plate 130 defines a posterior guide ramp 136 along each side rail 132, 134 and an anterior guide ramp 138 along each side rail 132, 134. The guide ramps 136 and 138 are laterally inward of the ramps 116, 118 such that the ramps 116, 118 may overlap the ramps 136, 138. Each posterior guide ramp 136 defines a groove 137 configured to receive a portion of a respective pivot member 190 and each anterior guide ramp 138 defines a groove 137 configured to receive a portion of a respective pivot member 200. As will be described hereinafter, the pivot members 190, 200 are pivotally connected to respective actuators 150, 170 and slide along the respective ramp 136, 138 as the plates 110, 130 expand or contract.

The anterior rail 133 defines at least one bone screw/anchor through hole 141, with two such holes 141 shown in the illustrated embodiment. A blocking screw hole 142 is positioned next to each through hole 141 and is configured to receive a blocking screw 124 which may be utilized to maintain the bone screw 250 or bone anchor 260 in the through hole 141. It will be appreciated that the bone screw 250 and bone anchor 260 may be used interchangeably in the respective holes 141 and may also be substituted with any other suitable fasteners. The anterior rail 133 also defines the second hemispherical portion 145 of the driver opening 143 as shown in FIG. 2. The posterior rail 131 defines the second hemispherical portion 147 of the seat for the spherical bearing 240. A receiving slot 146 extends next to the hemispherical portion 127 and is configured to receive a flange 246 of the other of the bearing members 241 that defines another portion of the spherical bearing 240.

Although anterior rails 113, 133 are shown with through holes 121, 141 configured to receive respective fasteners, it will be appreciated by one skilled in the art that the bore holes or through holes 121, 141 may be present in any suitable number and configuration for fixation. In the alternative, the bore holes or through holes 121, 141 may be omitted to provide a standalone device.

Figure 6:
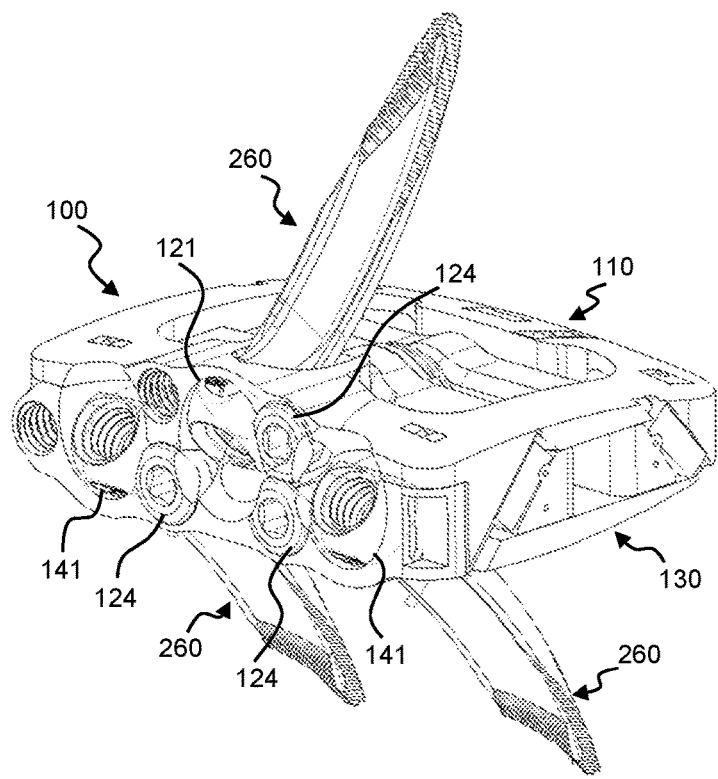
FIG. 6 is a perspective view of the implant of FIG. 1 in a compressed or reduced height configuration, together with three mounted bone anchors.
Figure 7:
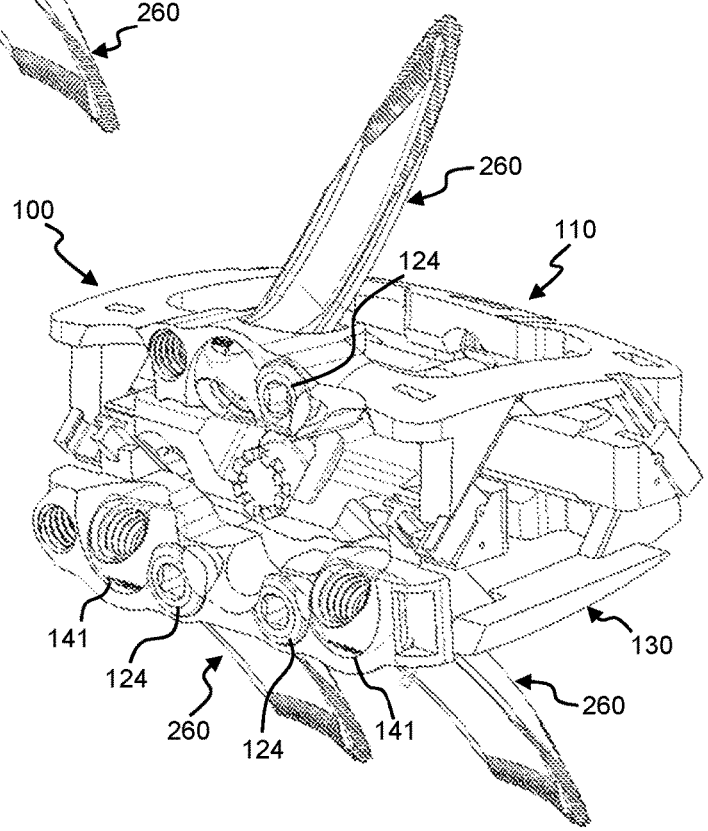
FIG. 7 is a perspective view of the implant of FIG. 1 in an expanded or increased height configuration, together with three mounted bone anchors.

While not shown, one or both of the end plates 110, 130 can be provided with teeth or other projections which can penetrate body tissue to reduce a likelihood of migration of implant 100 after implantation. Additionally, one or both of the end plates 110, 130 may be coated with or impregnated with therapeutic agents, including bone growth, healing, antimicrobial, or drug materials, which may be released at a therapeutic rate, using methods known to those skilled in the art. Additionally, while FIGS. 2-5 show bone screws 260 extending through the through holes 121, 141 for securing of the implant 100, the disclosure is not limited to such. For example, FIGS. 6 and 7 illustrate bone anchors 260 extending through the through holes 121, 141. Other anchoring elements may also be utilized. In each case, the through holes 121, 141 may have a concave opening such that the screws 250 or anchors 260 may be inserted into body tissue at an optimal angle with respect to implant 100, whereby optimal purchase may be obtained, or certain body tissue may be avoided.

Figure 4:
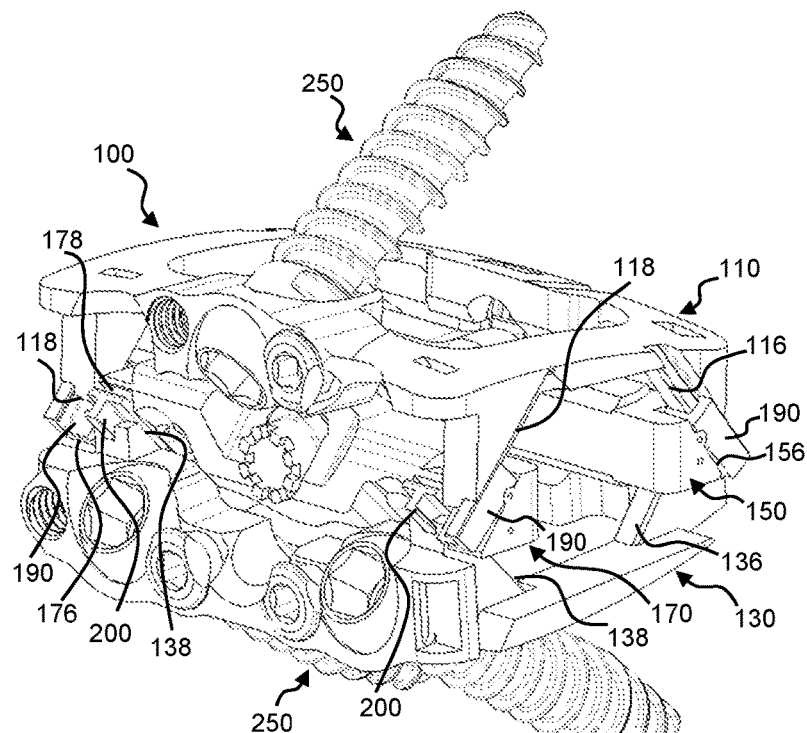
FIG. 4 is a perspective view of the implant of FIG. 1 in an expanded or increased height configuration, together with three mounted bone screws.
Figure 5:
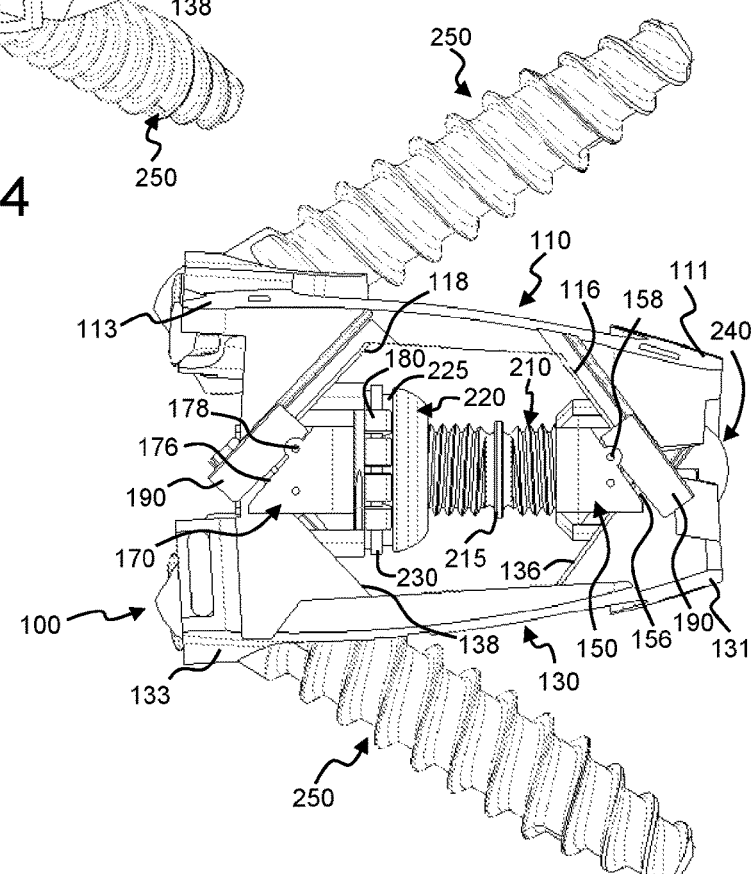
FIG. 5 is a side elevation view of the implant as shown in FIG. 4.

Implant 100 has a collapsed state or height, illustrated in FIGS. 2 and 3, and an expanded state or height, illustrated in FIGS. 4 and 5. Implants 100 of the disclosure may be inset into the intervertebral disc space at a collapsed height, and then expand axially (superior/inferior) to restore height loss in the disc space. The implant provides distraction as well as achieves optimal height restoration. When inserted in a collapsed state, implants 100 reduce impaction to tissue in the joint space during insertion, and form the least visually blocking or obstructing profile. Additionally, the lordotic angle of implant 100 may be adjusted to have an increased lordotic angle, illustrated in FIGS. 8 and 9, or a decreased lordotic angle, illustrated in FIGS. 10 and 11.

The anterior and posterior actuators 150, 170 are positioned between the plates 110, 130 and are moveable relative to the plates 110, 130 to control the separation between the plates 110, 130. The anterior actuator 150 is positioned between the plates 110, 130 proximate the anterior rails 111, 131. The anterior actuator 150 has a laterally extending body 152 with a central through passage 154 with internal threads 155 configured to threadably engage the actuator screw 210, as will be described hereinafter. An upper plate guiding ramp 156 is defined at each end of the body 152 and is configured to align with a respective anterior ramp 116 of the upper plate 110. Each of the upper plate guiding ramps 156 extends at the same incline angle as the opposing anterior ramp 116. Similarly, a lower plate guiding ramp 157 is defined inward of each end of the body 152 and is configured to align with a respective anterior ramp 136 of the lower plate 130. Each of the lower plate guiding ramps 157 extends at the same incline angle as the opposing anterior ramp 136. The body 152 defines pivot pin holes 158, 159 next to the guiding ramps 156, 157, respectively, for pivotal mounting of the pivot members 190.

The posterior actuator 170 is positioned between the plates 110, 130 proximate the posterior rails 113, 133. The anterior actuator 170 has a laterally extending body 172 with a central non-threaded through passage 174 configured to receive the actuator nut 220. A series of fingers 180 extend from the posterior side of the body 172 about the through passage 174 and are configured to engage and retain the actuator nut 220, as will be described hereinafter. An upper plate guiding ramp 176 is defined at each end of the body 172 and is configured to align with a respective posterior ramp 118 of the upper plate 110. Each of the upper plate guiding ramps 176 extends at the same incline angle as the opposing superior ramp 118. Similarly, a lower plate guiding ramp 177 is defined inward of each end of the body 172 and is configured to align with a respective superior ramp 138 of the lower plate 130. Each of the lower plate guiding ramps 177 extends at the same incline angle as the opposing superior ramp 138. The body 172 defines pivot pin holes 178, 179 next to the guiding ramps 176, 177, respectively, for pivotal mounting of the pivot members 190, 200.

Referring to FIG. 1, each of the pivot members 190 includes a guide surface 192 configured to engage and slide along a respective ramp 116, 118, 136. A groove engaging flange 194 extends from each guide surface 192 and is configured to engage within the respective ramp groove 117, 119, 137 to prevent separation from the respective ramp 116, 118, 136. The opposite side of each guide surface 192 defines a pivot slot 196 configured to align with respective pivot pin holes 158, 159, 178 such that a pivot pin (not shown) pivotally connects each pivot member 190 to a respective actuator 150, 170. The pivot members 200 are similar to the pivot members 190 and includes a guide surface 202 configured to engage and slide along a respective ramp 138. A groove engaging flange 204 extends from each guide surface 202, more centrally compared to the pivot member 190, and is configured to engage within the respective ramp groove 139 to prevent separation from the respective ramp 138. The opposite side of each guide surface 202 defines a pivot slot 206 configured to align with respective pivot pin holes 179 such that a pivot pin (not shown) pivotally connects each pivot member 200 to a respective actuator 170.

Figure 14:
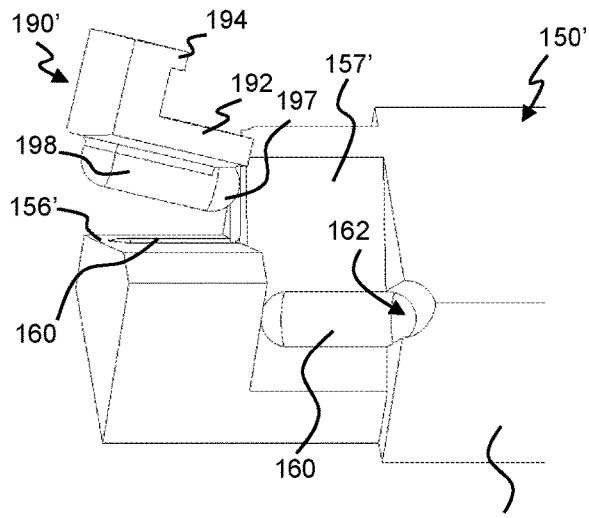
FIGS. 14-16 are expanded perspective views of a portion of an alternative actuator showing the sequential mounting of an alternative pivot member relative thereto.
Figure 15:
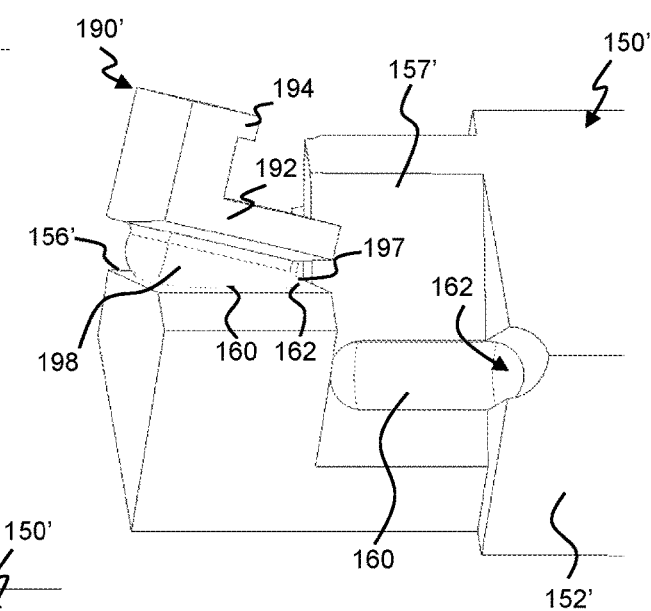
Figure 16:
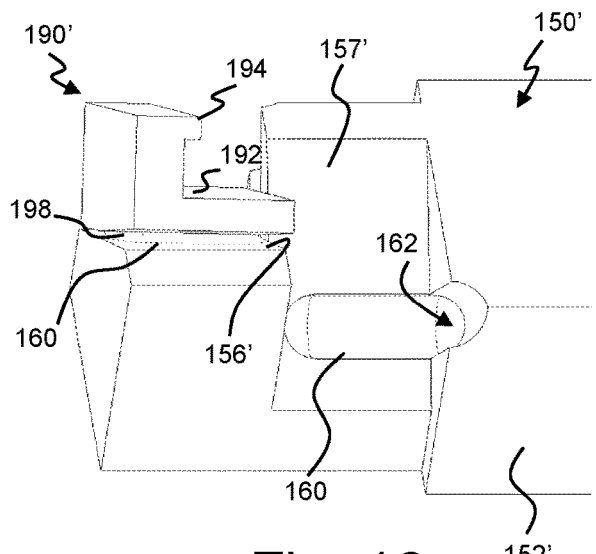

Referring to FIGS. 14-16, an alternative method of pivotally connecting the pivot members to the actuators will be described. While the figures show a posterior actuator 150', a similar construction may be provided for the anterior actuator. In the present embodiment, each of the ramps 156, 157 defines a pivot slot 160 with a portion 162 that extends laterally under a portion of the actuator body 152'. Instead of a pivot pin slot, each pivot member 190' has a rounded underside member 198 with an extending portion 197. The rounded underside member 198 fits into the pivot slot 160 with the extending portion 197 fitting into the portion 162 that extends laterally under a portion of the actuator body 152'. When fully placed as illustrated in FIG. 16, the pivot member 190' is retained in the actuator and is pivotal thereto.

The pivot members 190, 200 are pivotally connected to and thereby move with the respective actuator 150, 170 while also being engaged with the grooves 117, 119, 137, 139 in the upper and lower end plates 110, 130. As such, as the actuators 150, 170 are moved anteriorly or posteriorly, the pivot members 190, 200 slide along the ramps 116, 118, 136, 138 causing the end plates 110, 130 to move toward or away from one another. The pivoting nature of the pivot members 190, 200 allows the angle between the plates 110, 130 to be changed while maintaining the sliding relationship.

Figure 8:
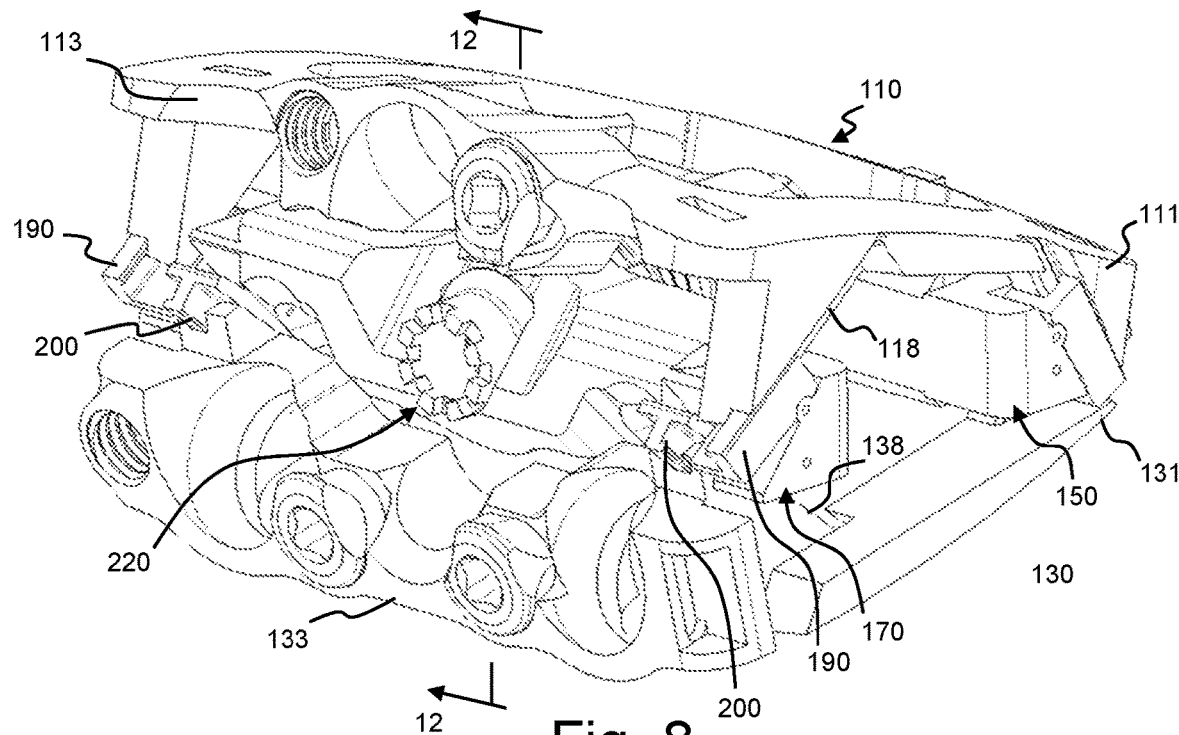
FIG. 8 is a perspective view of the implant of FIG. 1 in an expanded anterior or increased lordotic angle configuration.
Figure 9:
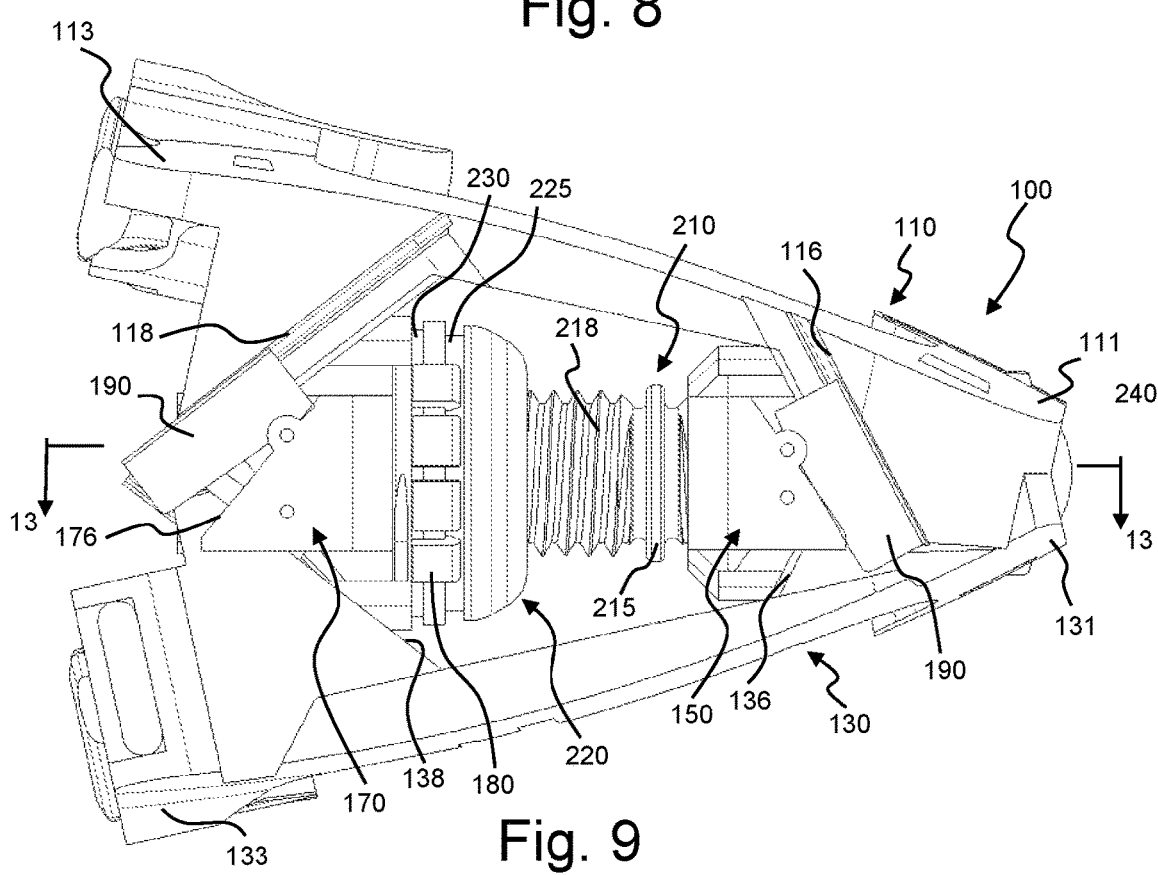
FIG. 9 is a side elevation view of the implant as shown in FIG. 8.
Figure 10:
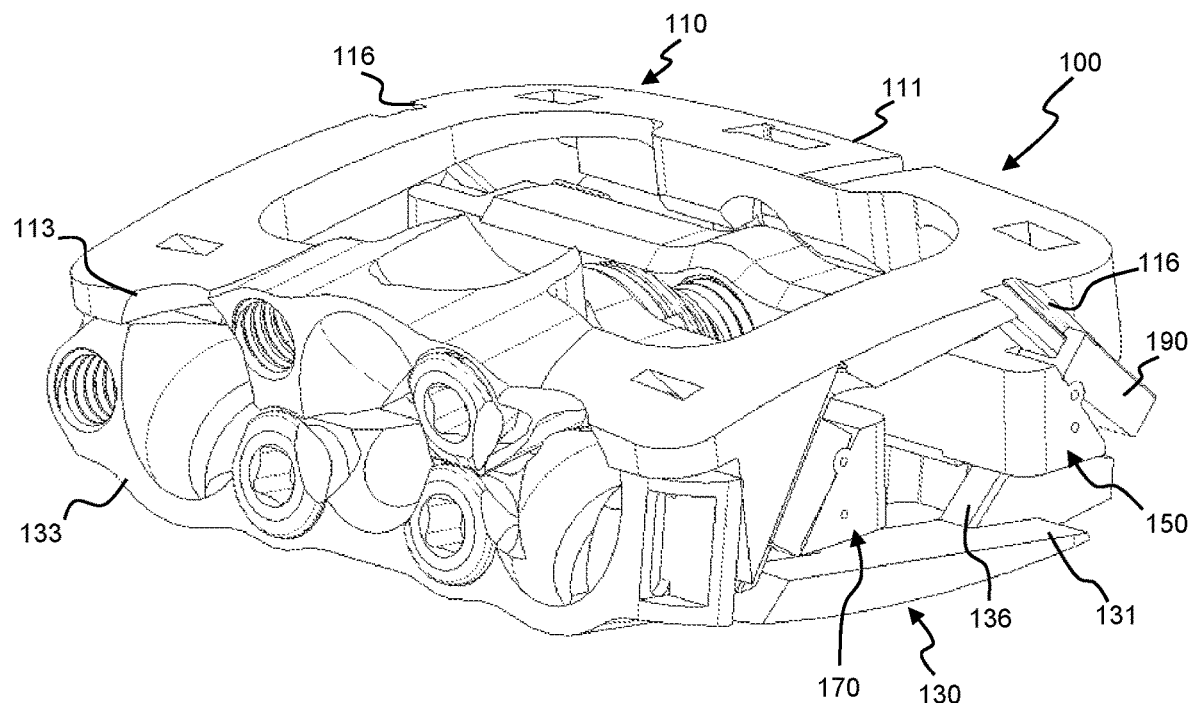
FIG. 10 is a perspective view of the implant of FIG. 1 in an expanded superior or decreased lordotic angle configuration.
Figure 11:
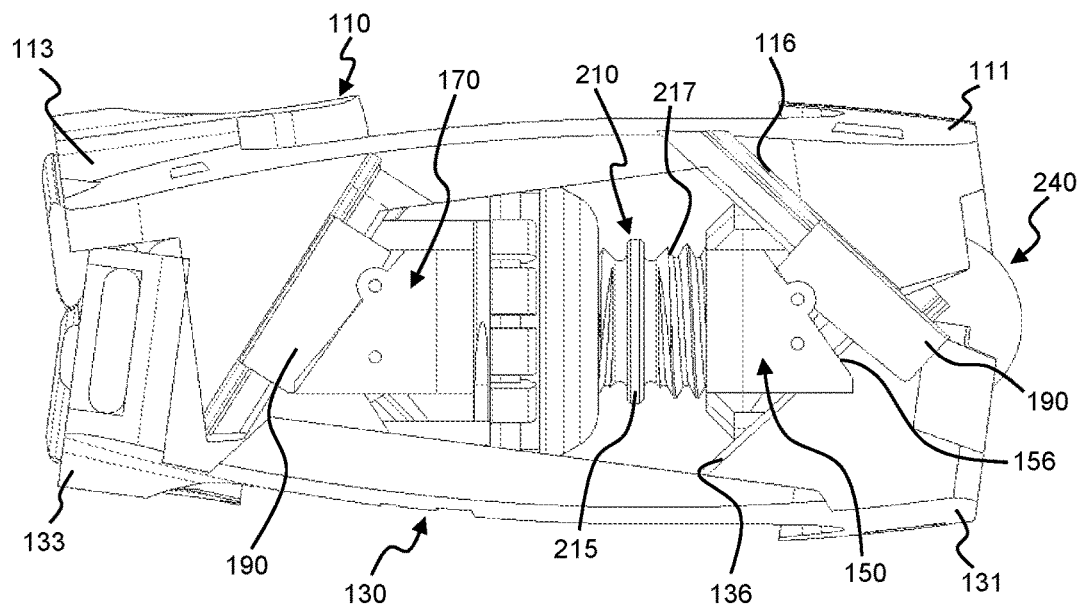
FIG. 11 is a side elevation view of the implant as shown in FIG. 10.

Movement of the actuators 150, 170 and the corresponding movement of the end plates 110, 130 will now be described. FIGS. 2 and 3 illustrate the end plates 110, 130 in the collapsed state and the actuators 150, 170 are both generally centrally located. To move the end plates 110, 130 to the expanded state, the anterior actuator 150 moves anteriorly and the posterior actuator 170 moves posteriorly, as shown in FIGS. 4 and 5. As the actuators 150, 170 move, the pivot members 190, 200 slide along the respective ramps 116, 118, 136, 138. In such expanding actuation, the actuators 150, 170 are moved at the same rate and therefore the end plates 110, 130 maintain the given angle between them and the pivot members 190, 200 generally do not pivot. If it is desired to increase the lordotic angle between the plates 110, 130, the anterior actuator 170 is moved anteriorly while the posterior actuator 150 remains stationary, as illustrated in FIGS. 8 and 9. As the anterior actuator 170 moves, the pivot members 190, 200 slide along the respective ramps 118, 138. Additionally, because the angle between the end plates 110, 130 changes, each of the pivot members 190, 200 pivots relative to its respective actuator 150, 170. Conversely, if it is desired to decrease the lordotic angle between the plates 110, 130, the posterior actuator 150 is moved posteriorly while the anterior actuator 170 remains stationary, as illustrated in FIGS. 10 and 11. As the posterior actuator 150 moves, the pivot members 190 slide along the respective ramps 116, 136. Again, because the angle between the end plates 110, 130 changes, each of the pivot members 190, 200 pivots relative to its respective actuator 150, 170.

Figure 12:
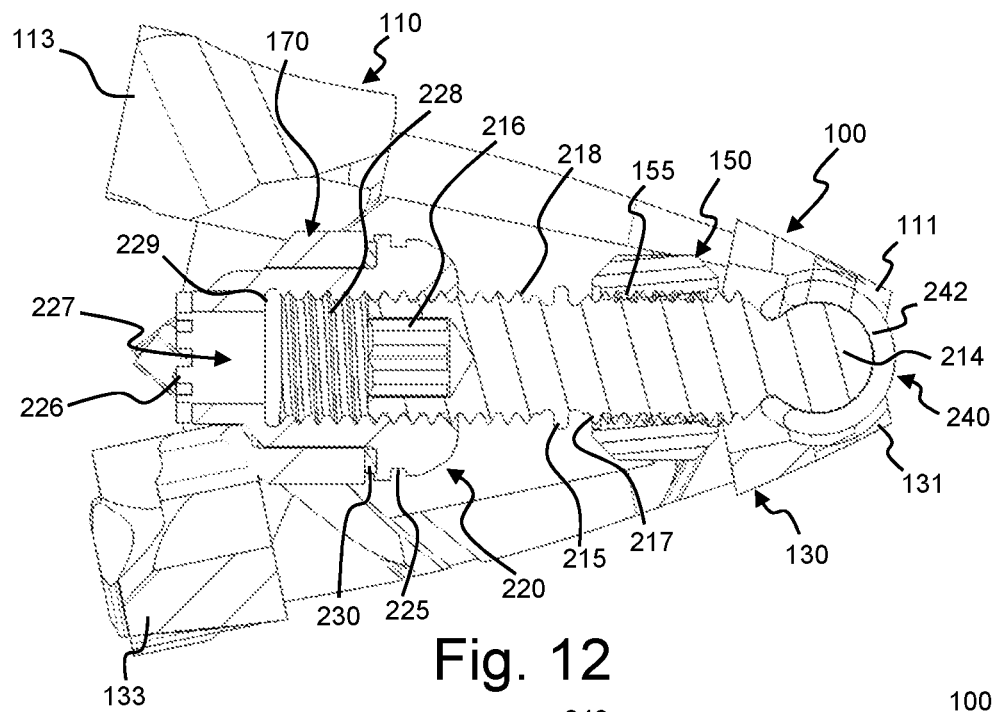
FIG. 12 is a cross-sectional view along the line 12-12 in FIG. 8.
Figure 13:
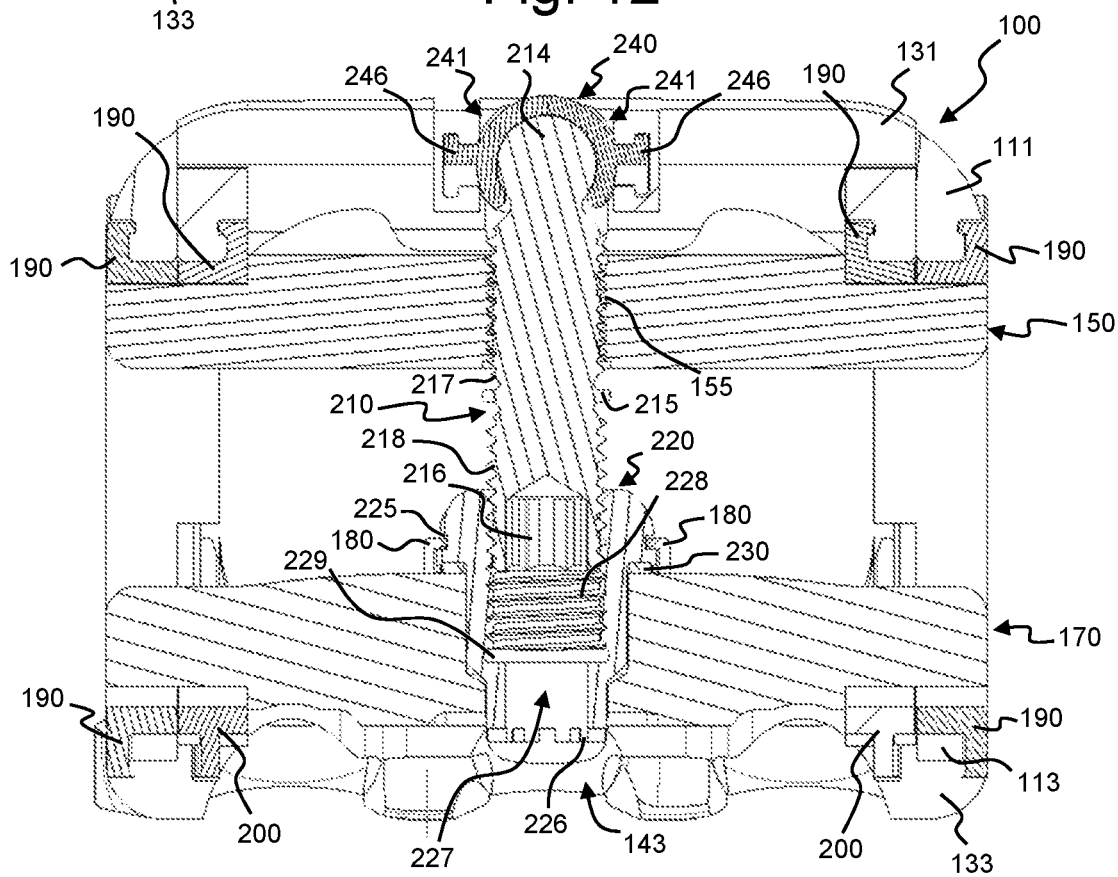
FIG. 13 is a cross-sectional view along the line 12-12 in FIG. 9.

To facilitate movement of the actuators 150, 170, an actuator assembly extends between the actuators 150, 170. Referring to FIGS. 1, 12 and 13, in the present embodiment, the actuator assembly includes an actuator screw 210, an actuator nut 220, and a spherical bearing 240. The actuator screw 210 includes a shaft extending between a posterior end 211 and an anterior end 213. The posterior end 211 of the screw 210 has a ball 214 while the anterior end 213 includes a driver receiver 216. The actuator screw 210 has a first set of threads 217 on the anterior end and a second set of threads 218 on the posterior end with a flange 215 in between. The first and second sets of threads 217, 218 are oppositely handed, i.e. one set is right handed while the other set is left handed. The posterior end 211 of the actuator screw 210 extends through the central through passage 154 of the posterior actuator 150 with the with threads 217 engaged with the internal threads 155.

The ball 214 of the actuator screw 210 extends beyond the posterior actuator 150 and is retained in the spherical bearing 240. In the present embodiment, the spherical bearing 240 is defined by opposed bearing members 241. With reference to FIG. 1, each bearing member 241 has a generally hemispherical bearing surface 242. An arm 244 extends between the bearing surface 242 and a mounting flange 246. Each mounting flange 246 is configured to be received in a respective receiving slot 126, 146 of the upper end plate 110 or the lower end plate 130. With the ball 214 retained between the bearing surfaces 242 and the flanges 246 engaged with the respective end plates 110, 130, the actuator screw 210 is axially fixed relative to the end plates 110, 130 but is free to pivot relative thereto. As such, as the posterior actuator 150 moves along the thread set 217 of the actuator screw 210, the posterior actuator 150 moves relative to the end plates 110, 130.

The actuator nut 220 has a body 222 extending between a posterior end 221 and an anterior end 223. A through passage 227 extends through the body 222 from the anterior end 223 to the posterior end 221. A portion of through passage 227 defines internal threads 228 which are configured to threadably engage the second thread set 218 of the actuator screw 210. A shoulder 229 is defined within the through passage 227 to define a stop for the actuator screw 210. The anterior end 223 of the actuator nut 220 defines a driver engagement 226 about the through passage 227, which in the illustrated embodiment is a series of notches and teeth.

The anterior end 223 of the body 222 of the actuator nut 220 is configured to be received into the non-threaded through passage 174 of the anterior actuator 170. A radial flange 224 extending from the body 222 limits the extent the actuator nut 220 moves into the non-threaded through passage 174. A thrust washer 230 may be positioned between the flange 224 and the anterior actuator 170. A groove 225 is defined in the actuator nut body 222 posteriorly of the flange 224. The fingers 180 extending from the anterior actuator 170 are configured to engage the groove 225 such that the actuator nut 220 is connected to the anterior actuator 170.

The actuator assembly provides three modes of operation. In the first mode of operation, the actuator screw 210 is turned via the driver receiver 216 while the actuator nut 220 is not turned. Engagement of the internal threads 155 of posterior actuator 150 with the first set of threads 217 of the turning actuator screw 210 causes the posterior actuator 150 to move, for example posteriorly. At the same time, since the opposite handed threads 218 of the turning actuator screw 210 are engaging the internal threads 218 of the non-turning actuator nut 220, the actuator nut 220, and thereby the anterior actuator 170, are caused to move in the opposite direction, in this example, anteriorly. This results in both actuators 150, 170 moving toward the ends of the end plates 110, 130 and gives linear expansion with both endplates 110, 130 expanding the same distance (FIGS. 4 and 5). Turning the actuator screw 210 in the opposite direction would move the end plates 110, 130 toward one another.

In the second mode of operation, the actuator screw 210 is not turned while the actuator nut 220 is turned via the driver engagement 226. Since the actuator screw 210 is not turning, the posterior actuator 150 does not move. However, as the actuator nut 220 turns relative to the thread set 218 of the stationary actuator screw 210, the actuator nut 220, and thereby the anterior actuator 170, move alone which expands the anterior end of each endplate only and results in an increase in lordotic angle. (FIGS. 8 and 9). Turning the actuator nut 220 in the opposite direction would move the anterior ends of end plates 110, 130 toward one another.

In the third mode of operation, the actuator screw 210 is turned via the driver receiver 216 while the actuator nut 220 is also turned via the driver engagement 226. Since the actuator screw 210 and the actuator nut 220 are turning at the same rate, there is no relative movement between the actuator nut 220 and the actuator screw 210. As such, the anterior actuator 170 does not move. However, the turning actuator screw 210 causes the posterior actuator 150 to move alone which expands the posterior end of each endplate only and results in a reduction in lordosis. (FIGS. 10 and 11). Turning the actuator screw and actuator nut 220 simultaneously in the opposite direction would move the posterior ends of end plates 110, 130 toward one another.

Devices of the disclosure provide for adjacent vertebrae to be supported during flexion/extension, lateral bending, and axial rotation. In one embodiment, implant 100 is indicated for spinal arthroplasty in treating skeletally mature patients with degenerative disc disease, primary or recurrent disc herniation, spinal stenosis, or spondylosis in the lumbosacral spine (LI-SI). Degenerative disc disease is advantageously defined as discogenic back pain with degeneration of the disc confirmed by patient history and radiographic studies, with or without leg (radicular) pain. Patients may be advantageously treated, for example, who may have spondylolisthesis up to grade 1 at the involved level. The surgery position implant 100 may be performed through an anterior, anterolateral, posterolateral, and/or lateral approach. Various implant methods are disclosed in US 2014/0277489, the contents of which are incorporated herein by reference in its entirety for all purposes. During implantation, the driver receiver 216 and driver engagement 226 may be engaged by separate tools or an integrated tool to actuate the actuator assembly.

While the present disclosure has been described in terms of exemplary aspects, those skilled in the art will recognize that the present disclosure can be practiced with modifications in the spirit and scope of the appended claims. These examples given above are merely illustrative and are not meant to be an exhaustive list of all possible designs, aspects, applications or modifications of the present disclosure.

What is claimed is:

1. An implant for therapeutically separating bones of a joint, the implant comprising:
a first endplate extending between an anterior end and a posterior end, the first endplate having a bone engaging surface on one side, and anterior and posterior ramped surfaces on the other side;
a second endplate extending between an anterior end and a posterior end, the second endplate having a bone engaging surface;
a posterior actuator coupled between the first and second endplates, the posterior actuator having a posterior guiding surface slidably coupled to the posterior ramped surface of the first endplate;
an anterior actuator coupled between the first and second endplates, and positioned anteriorly from the posterior actuator, the anterior actuator having an anterior guiding surface slidably coupled to the anterior ramped surface of the first endplate;
an actuator driver assembly having a posterior driver threadably engaged with the posterior actuator and an anterior driver threadably engaged with the posterior driver and rotatably coupled to the anterior actuator, selective rotation of the anterior and posterior drivers causing an independent movement of the anterior and posterior actuators to cause an independent movement of the anterior and posterior ends of the first endplate relative to the second endplate.

2. The implant of claim 1, wherein:
the posterior driver includes an actuator screw having a first external thread set proximate the posterior end and a second external thread set proximate the anterior end; and
the anterior driver includes an actuator nut having a through passage defining an internal thread within the through passage, the internal thread threadably engaged with the second external thread set, wherein the actuator nut is axially fixed relative to the anterior actuator but rotatable relative thereto.

3. The implant of claim 2, wherein the first and second external thread sets are oppositely handed.

4. The implant of claim 1, wherein the posterior end of the posterior driver includes a ball which is supported in a spherical bearing supported by the first and second endplates.

5. The implant of claim 2, wherein the anterior end of the actuator screw is sized and shaped to receive a driver.

6. The implant of claim 1, wherein the anterior driver includes a body having a radial flange received in a through passage of the anterior actuator.

7. The implant of claim 6, wherein the anterior end of the body is configured to receive a driver engagement about the anterior actuator through passage.

8. The implant of claim 1, wherein:
the anterior driver includes a body having a radial flange received in a through passage of the anterior actuator; and
the implant further comprising a thrust washer positioned between the radial flange and the anterior actuator.

9. The implant of claim 1, wherein:
the anterior driver includes a body having a radial flange received in a through passage of the anterior actuator; and
the anterior actuator includes a plurality of fingers that engage a groove in the anterior actuator posteriorly of the flange.

10. The implant of claim 1, wherein an insertion driver is adapted to independently rotate the anterior driver and the posterior driver, wherein the actuator driver assembly is operable in at least three modes including:
a first mode wherein the posterior driver is rotated while the anterior driver is not rotated such that the posterior and anterior ends of both endplates move away from each other the same distance;
a second mode wherein the posterior driver is not rotated while the anterior driver is rotated such that the anterior actuator moves alone which expands the anterior end of the first endplate relative to the second endplate; and
a third mode wherein the anterior driver and posterior driver are rotated simultaneously which moves the posterior actuator only resulting in expansion of the posterior end of the first endplate relative to the second endplate.

11. The implant of claim 1, wherein:
the posterior driver includes an actuator screw having a first external thread set proximate the posterior end and a second external thread set proximate the anterior end, wherein the posterior end of the actuator screw extends through and the first external thread set threadably engages a through passage in the posterior actuator;
the anterior driver includes an actuator nut having a through passage defining an internal thread within the through passage, the internal thread threadably engaged with the second external thread set, wherein the actuator nut is axially fixed relative to the anterior actuator but rotatable relative thereto; and
wherein the actuator screw includes a flange disposed between the first and second external thread sets, the flange adapted to stop the anterior actuator from moving posteriorly of the flange.

12. The implant of claim 1, wherein:
the posterior actuator includes a posterior pivot member pivotally connected to the posterior guiding surface and in sliding engagement with the first endplate posterior ramped surface;
the anterior actuator includes an anterior pivot member pivotally connected to the anterior guiding surface and in sliding engagement with the first endplate anterior ramped surface.

13. An implant for therapeutically separating bones of a joint, the implant comprising:
a first endplate having a bone engaging surface on one side, and anterior and posterior ramped surfaces on the other side;
a second endplate having a bone engaging surface;
a posterior actuator positioned between the first and second endplates and having a posterior guiding surface slidably coupled to the posterior ramped surface of the first endplate;
an anterior actuator positioned between the first and second endplates, and positioned anteriorly from the posterior actuator, the anterior actuator having an anterior guiding surface slidably coupled to the anterior ramped surface of the first endplate;
an actuator driver assembly including:
an anterior driver coupled to the anterior actuator and adapted to move the anterior end of the first endplate relative to the second endplate when the anterior driver is rotated;
a posterior driver coupled to the posterior actuator and adapted to move the posterior end of the first endplate relative to the second endplate when the posterior driver is rotated.

14. The implant of claim 13, wherein:
the posterior driver is threadably engaged with the posterior actuator; and
the anterior driver is threadably engaged with the posterior driver and rotatably coupled to the anterior actuator, selective rotation of the anterior and posterior drivers causing an independent movement of the anterior and posterior actuators to cause an independent movement of the anterior and posterior ends of the first endplate relative to the second endplate.

15. The implant of claim 14, wherein an insertion driver is adapted to independently rotate the anterior driver and the posterior driver, wherein the actuator driver assembly is operable in at least three modes including:
a first mode wherein the posterior driver is rotated while the anterior driver is not rotated such that the posterior and anterior ends of both endplates move away from each other the same distance;
a second mode wherein the posterior driver is not rotated while the anterior driver is rotated such that the anterior actuator moves alone which expands the anterior end of the first endplate relative to the second endplate; and
a third mode wherein the anterior driver and posterior driver are rotated simultaneously which moves the posterior actuator only resulting in expansion of the posterior end of the first endplate relative to the second endplate.

16. The implant of claim 14, wherein:
the posterior driver includes an actuator screw having a first external thread set proximate the posterior end and a second external thread set proximate the anterior end; and
the anterior driver includes an actuator nut having a through passage defining an internal thread within the through passage, the internal thread threadably engaged with the second external thread set, wherein the actuator nut is axially fixed relative to the anterior actuator but rotatable relative thereto.

17. The implant of claim 13, wherein the posterior end of the posterior driver includes a retainer shaped to be retained in a bearing supported by the first and second endplates.

18. The implant of claim 13, wherein the anterior driver includes a body having a radial flange received in a through passage of the anterior actuator.

19. The implant of claim 13, wherein:
the anterior driver includes a body having a radial flange received in a through passage of the anterior actuator; and
the anterior actuator includes a plurality of fingers that engage a groove in the anterior actuator posteriorly of the flange.

20. The implant of claim 13, wherein:
the posterior actuator includes a posterior pivot member pivotally connected to the posterior guiding surface and in sliding engagement with the first endplate posterior ramped surface;
the anterior actuator includes an anterior pivot member pivotally connected to the anterior guiding surface and in sliding engagement with the first endplate anterior ramped surface.

* * * * *